United States Patent
Stiles

(10) Patent No.: US 8,335,552 B2
(45) Date of Patent: Dec. 18, 2012

(54) METHOD AND APPARATUS FOR INSTRUMENT PLACEMENT

(75) Inventor: David Stiles, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 353 days.

(21) Appl. No.: 12/431,108

(22) Filed: Apr. 28, 2009

(65) Prior Publication Data

US 2010/0240986 A1 Sep. 23, 2010

Related U.S. Application Data

(60) Provisional application No. 61/161,904, filed on Mar. 20, 2009.

(51) Int. Cl.
*A61B 5/00* (2006.01)

(52) U.S. Cl. ........ 600/407; 600/411; 600/416; 600/424; 600/427; 600/439; 600/461; 382/128; 382/131

(58) Field of Classification Search .................. 600/411, 600/416, 420, 424, 427, 439, 461; 382/128, 382/131
See application file for complete search history.

(56) References Cited

U.S. PATENT DOCUMENTS

| | | | |
|---|---|---|---|
| 5,592,939 A | 1/1997 | Martinelli | |
| 5,720,720 A | 2/1998 | Laske et al. | |
| 5,913,820 A | 6/1999 | Bladen et al. | |
| 5,983,126 A | 11/1999 | Wittkampf | |
| 6,118,845 A | 9/2000 | Simon et al. | |
| 6,201,988 B1 * | 3/2001 | Bourland et al. | 600/427 |
| 6,381,485 B1 | 4/2002 | Hunter et al. | |
| 6,390,097 B1 | 5/2002 | Chandra | |
| 6,402,762 B2 | 6/2002 | Hunter et al. | |
| 6,474,341 B1 | 11/2002 | Hunter et al. | |
| 6,482,182 B1 | 11/2002 | Carroll et al. | |
| 6,493,573 B1 | 12/2002 | Martinelli et al. | |
| 6,516,212 B1 | 2/2003 | Bladen et al. | |
| 6,591,004 B1 | 7/2003 | VanEssen et al. | |
| 6,697,534 B1 | 2/2004 | Tan et al. | |
| 6,850,793 B1 | 2/2005 | Miyazaki et al. | |
| 6,905,492 B2 * | 6/2005 | Zvuloni et al. | 606/21 |
| 7,081,088 B2 * | 7/2006 | Geiger | 345/427 |
| 7,167,180 B1 | 1/2007 | Shibolet | |
| 7,190,163 B2 | 3/2007 | Rajagopalan et al. | |
| 7,217,276 B2 | 5/2007 | Henderson et al. | |
| 7,542,791 B2 | 6/2009 | Mire et al. | |
| 7,555,331 B2 | 6/2009 | Viswanathan | |
| 7,623,736 B2 | 11/2009 | Viswanathan | |
| 7,657,075 B2 | 2/2010 | Viswanathan | |
| 7,756,308 B2 | 7/2010 | Viswanathan | |

(Continued)

OTHER PUBLICATIONS

Wood et al. Technologies for Guidance of Radiofrequency Ablation in the Multimodality Interventional Suite of the Future. J Vasc Interv Radiol. Jan. 2007 ; 18(1 Pt 1): 9-24. doi:10.1016/j.jvir.2006.10.013.*

(Continued)

*Primary Examiner* — Brian Casler
*Assistant Examiner* — Phong K Huynh
(74) *Attorney, Agent, or Firm* — Harness, Dickey & Pierce, PLC

(57) ABSTRACT

When delivering a therapy to a patient, such as a drug to a brain of a patient, an optimized delivery point can be selected. The optimized point can be based on physics, physiology, and pharmacology. The optimized point can be used for planning a surgical navigation procedure.

28 Claims, 9 Drawing Sheets

U.S. PATENT DOCUMENTS

| | | |
|---|---|---|
| 7,840,256 B2 | 11/2010 | Lakin et al. |
| 2003/0114752 A1 | 6/2003 | Henderson et al. |
| 2004/0215071 A1 | 10/2004 | Frank et al. |
| 2005/0004617 A1 | 1/2005 | Dawant et al. |
| 2005/0049486 A1 | 3/2005 | Urquhart et al. |
| 2005/0085714 A1 | 4/2005 | Foley et al. |
| 2005/0085720 A1 | 4/2005 | Jascob et al. |
| 2005/0171558 A1 | 8/2005 | Abovitz et al. |
| 2005/0267360 A1 | 12/2005 | Birkenbach et al. |
| 2006/0084867 A1 | 4/2006 | Tremblay et al. |
| 2006/0235483 A1 | 10/2006 | Schwan |
| 2007/0100226 A1* | 5/2007 | Yankelevitz et al. ......... 600/407 |
| 2007/0156453 A1 | 7/2007 | Frielinghaus et al. |
| 2007/0167788 A1 | 7/2007 | Hartlep et al. |
| 2007/0244387 A1 | 10/2007 | Rodriguez Ponce et al. |
| 2007/0249911 A1 | 10/2007 | Simon |
| 2007/0276340 A1 | 11/2007 | Poston et al. |
| 2008/0081982 A1 | 4/2008 | Simon et al. |
| 2008/0097187 A1 | 4/2008 | Gielen et al. |
| 2008/0097287 A1 | 4/2008 | Nelson et al. |
| 2008/0123921 A1 | 5/2008 | Gielen et al. |
| 2008/0123922 A1 | 5/2008 | Gielen et al. |
| 2008/0123923 A1 | 5/2008 | Gielen et al. |
| 2008/0132909 A1 | 6/2008 | Jascob et al. |
| 2009/0259230 A1 | 10/2009 | Khadem et al. |

OTHER PUBLICATIONS

Butz et al. Pre- and Intra-operative Planning and Simulation of Percutaneous Tumor Ablation, Proceedings of the Third International Conference on Medical Image Computing and Computer-Assisted Intervention, p. 317-326, Oct. 11-14, 2000.*

Tzafriri et al. "Mathematical Modeling and Optimization of Drug Delivery from Intratumorally-Injected Microspheres". Clinical Cancer Research vol. 11, 826-834, Jan. 15, 2005.*

Champleboux et al., "Accurate Calibration of Cameras and Range Imaging Sensors: the NPBS Method," IEEE International Conference on Robotics and Automation, Nice, France, May 1992.

Schueler et al., "Correction of Image Intensifier Distortion for Three-Dimensional X-Ray Angiography," SPIE Medical Imaging 1995, vol. 2432, pp. 272-279.

"Cranial Oncology Procedure Solutions and Benefits," Medtronic, 2 pages, http://www.medtronicnavigation.com/procedures/cranial/cranial_oncology.jsp, printed Mar. 13, 2008.

Hadani et al., Novel, Compact, Intraoperative Magnetic Resonance Imaging-guided System for Conventional Neurosurgical Operating Rooms, Neurosurgery, vol. 48, No. 4, Apr. 2001.

* cited by examiner

METHOD AND APPARATUS FOR INSTRUMENT PLACEMENT

CROSS-REFERENCE TO RELATED APPLICATIONS

This application claims the benefit and priority of 61/161,904, filed on Mar. 20, 2009. The entire disclosure of the above application is incorporated herein by reference.

FIELD

The present disclosure relates to surgical procedures, particularly relates to a system to assist in a neurological procedure.

BACKGROUND

This section provides background information related to the present disclosure which is not necessarily prior art.

During a neurological procedure a surgical instrument can be positioned within a neurological region of the patient. For example, an instrument can be positioned within a brain of a patient. Once the instrument is positioned within the brain, a therapy can be carried out on the patient. The therapy can include a delivery of a drug, delivery of an electrical stimulation, or other appropriate procedures.

A position within a neurological organ, such as the brain, may be difficult to determine based upon selected anatomical imaging techniques. For example, planar radiographs of a patient provide only two-dimensional image data of a patient. Two dimensional image data of the patient, however, alone may be difficult to interpret to identify a three-dimensional space or position. Nevertheless, the delivery of a therapy to a patient may be selected based upon a three-dimensional position or volume of the patient.

SUMMARY

This section provides a general summary of the disclosure, and is not a comprehensive disclosure of its full scope or all of its features.

To overcome the limitation of two-dimensional image data an optimized point can be pre-determined in pre-acquired image data. The optimized point can include a three-dimensional position that is determined by a method, as discussed herein. The identified point can then be used to navigate or guide an instrument to the identified optimized point. The optimized point can be optimized based on selected characteristics, as discussed herein.

Image data can be acquired of a patient that includes three-dimensional information or volume information of the patient. For example, a magnetic resonance imager (MRI) can be used to acquire 3D image data of the patient. Other three-dimensional image data can include a computed tomography (CT) scan, a reconstructed x-ray image, and other appropriate imaging modalities. The image data acquired with the selected imaging modality can be used to identify a specific three-dimensional position or location within the image data. The image data that defines an image space can be registered to a patient space defined by a patient. The registration can allow the position identified in the image data to be translated to a physical position in the patient space relative to the patient.

The specific location, which can be an optimized position within the image data, can be based upon a selected algorithm or automatic selection process. The automatic selection process can be used to identify a position within the image data for a specific purpose. For example, an algorithm can be used to identify a position within a three-dimensional volume including selected attributes or characteristics. The position within the three-dimensional volume can then be presented to a user, such as a surgeon, with a display device during and/or prior to a procedure. The surgeon can use the optimized point as a planning or starting point or disregard the point for various reasons. In addition, an instrument that is used during a procedure can be tracked and navigated to a selected position, such as the optimized position identified with the algorithm.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2B:
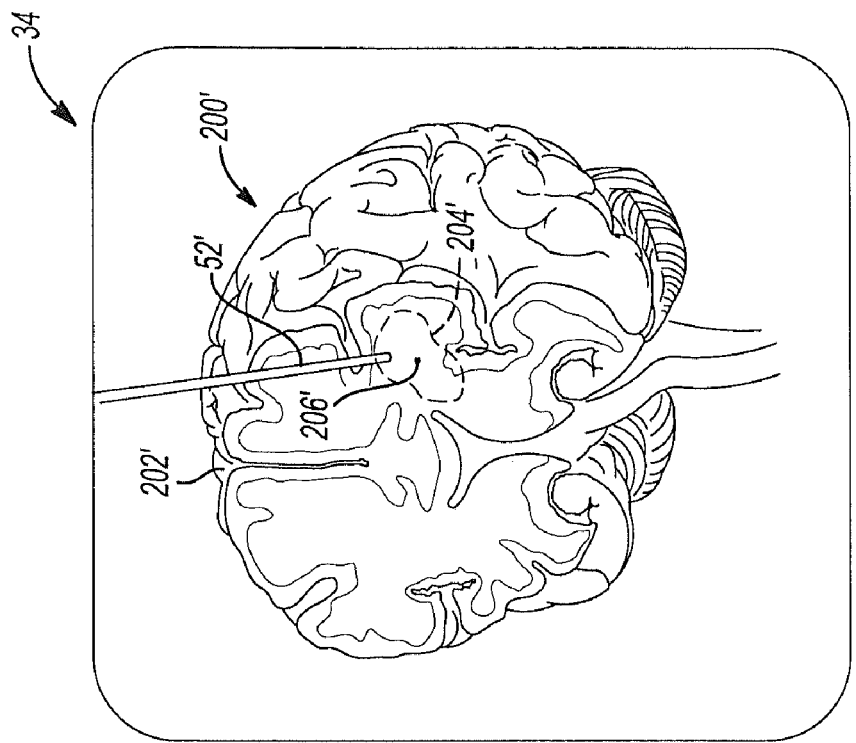
FIG. 2B is an illustration of image data of a brain.
Figure 2A:
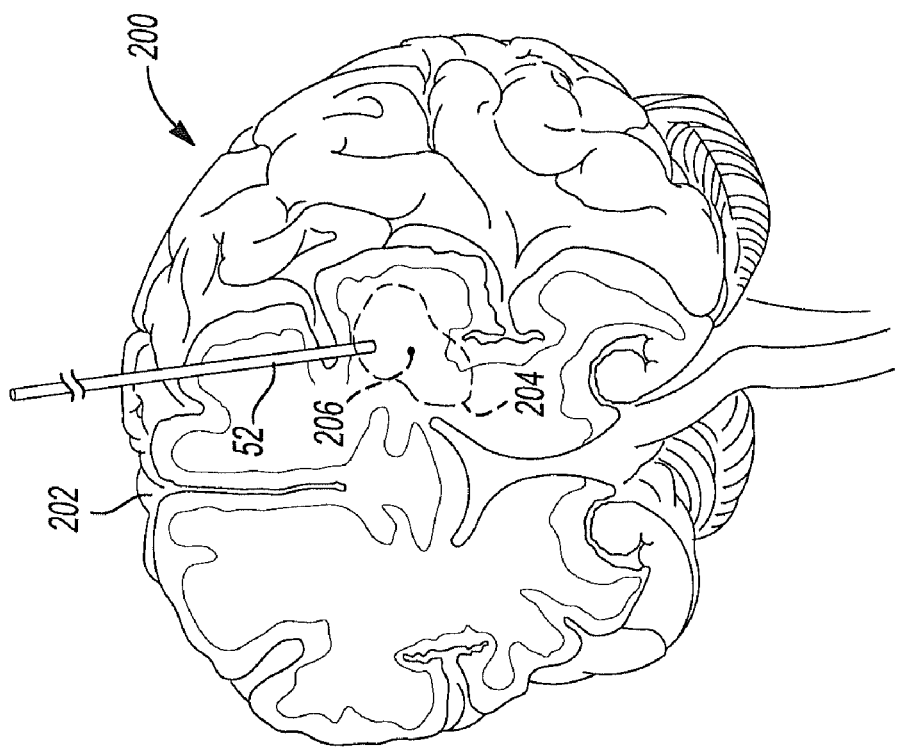
FIG. 2A is a schematic illustration of a brain illustrating three-dimensions of the brain.
Figure 2B:
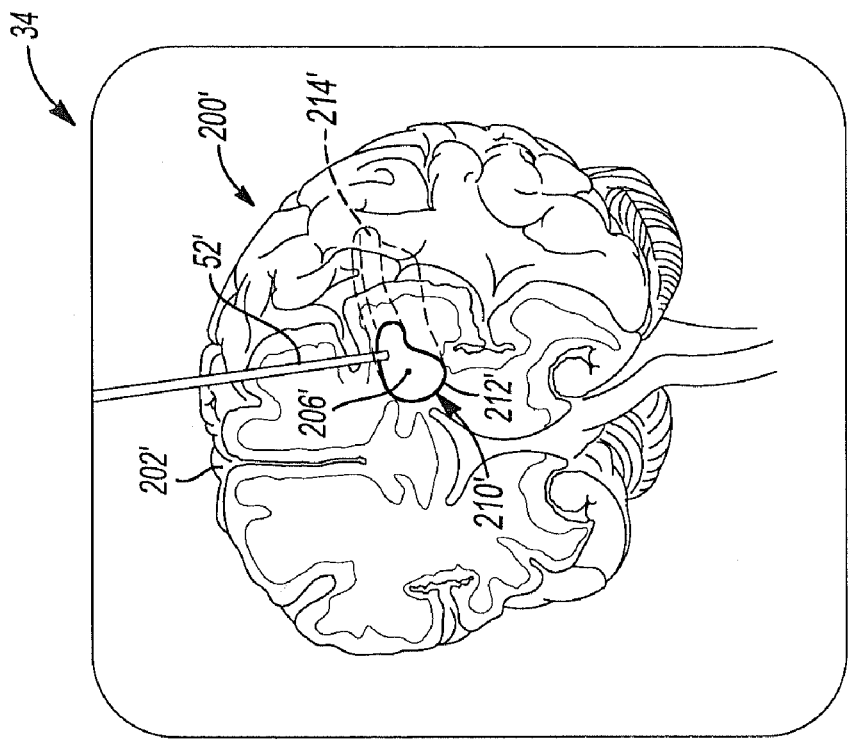
Figure 2A:
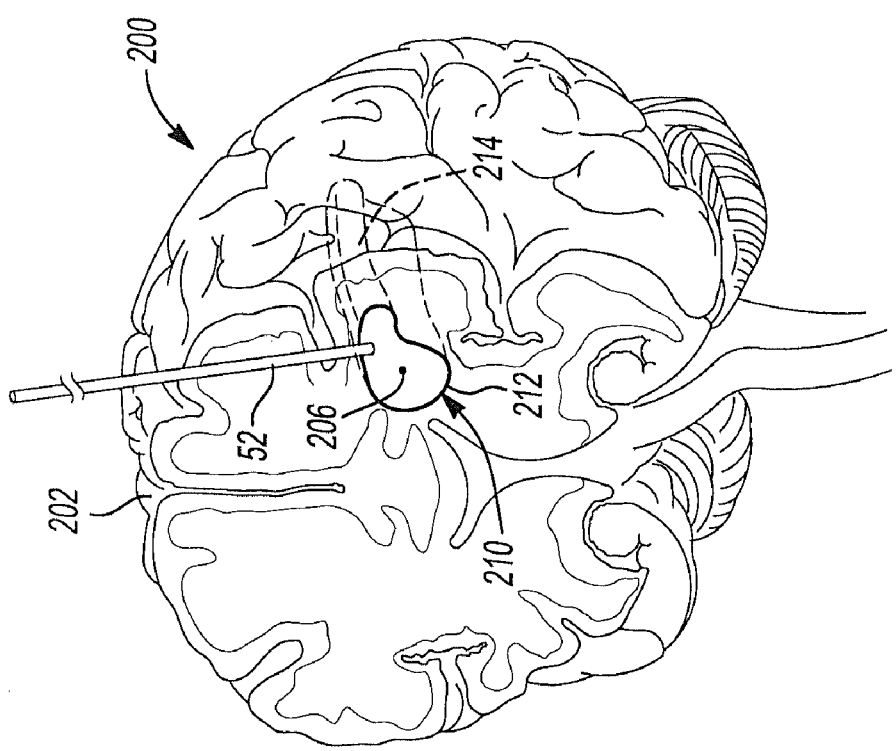
Figure 3:
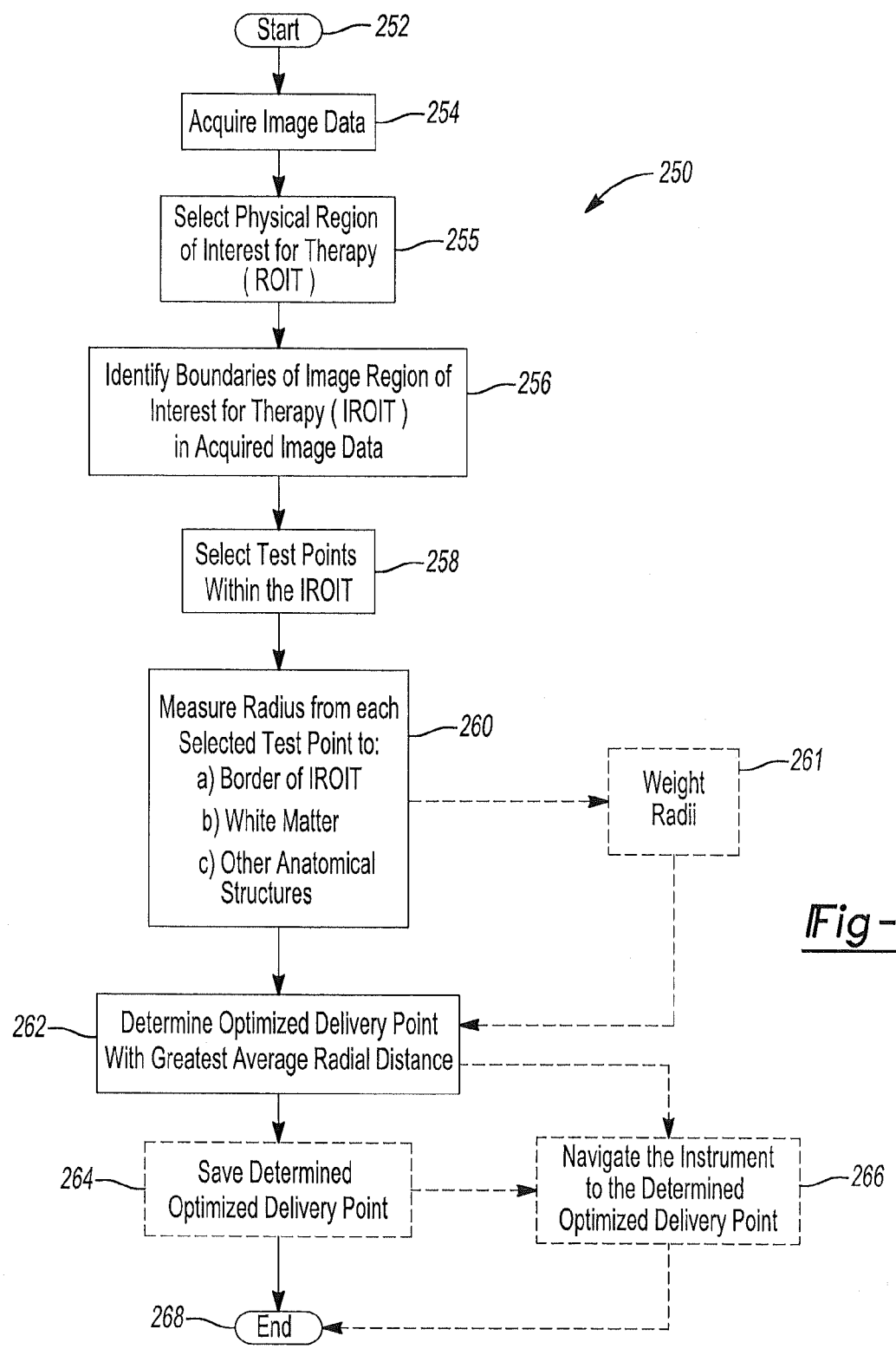
Figure 3A:
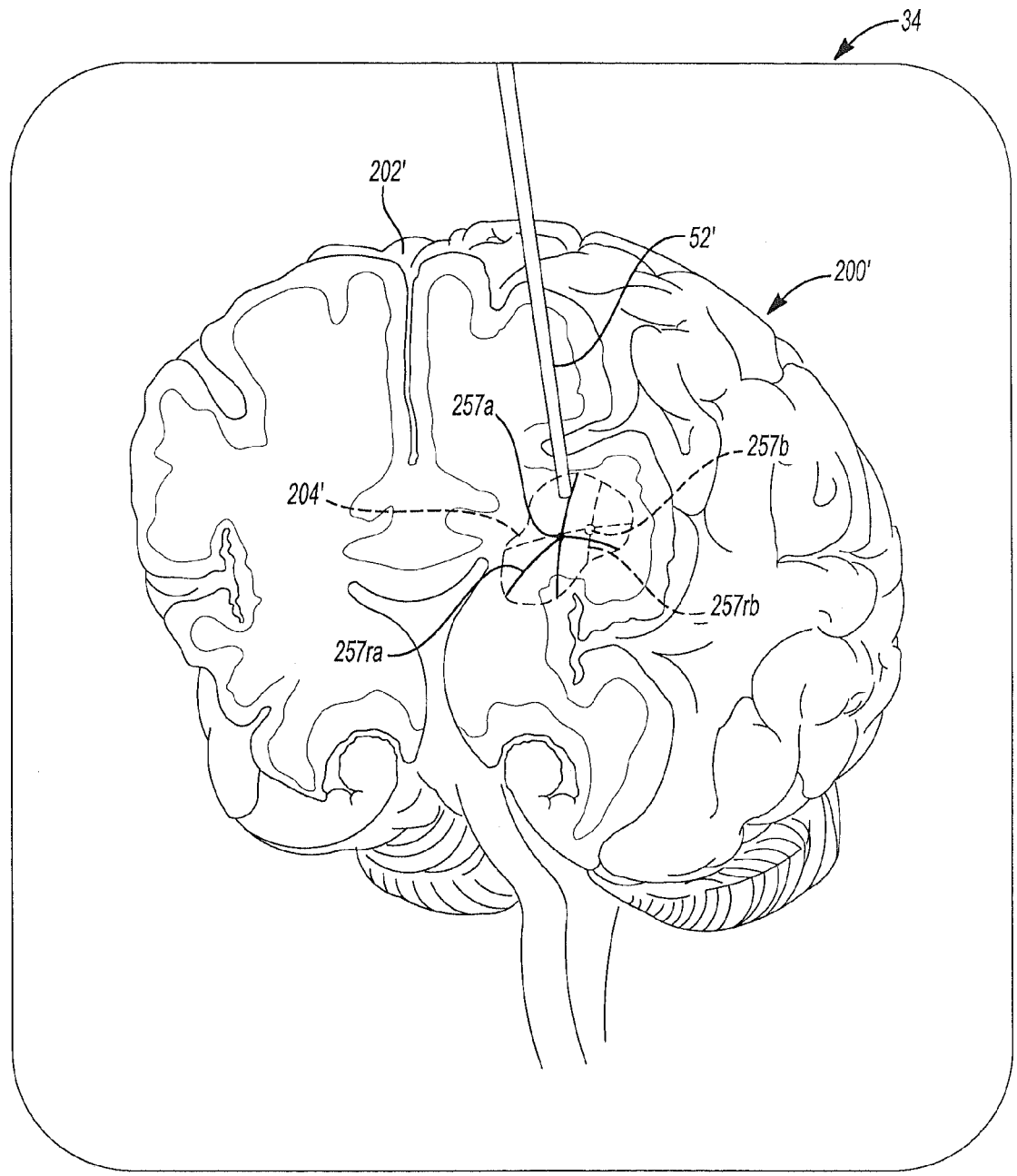
Figure 4:
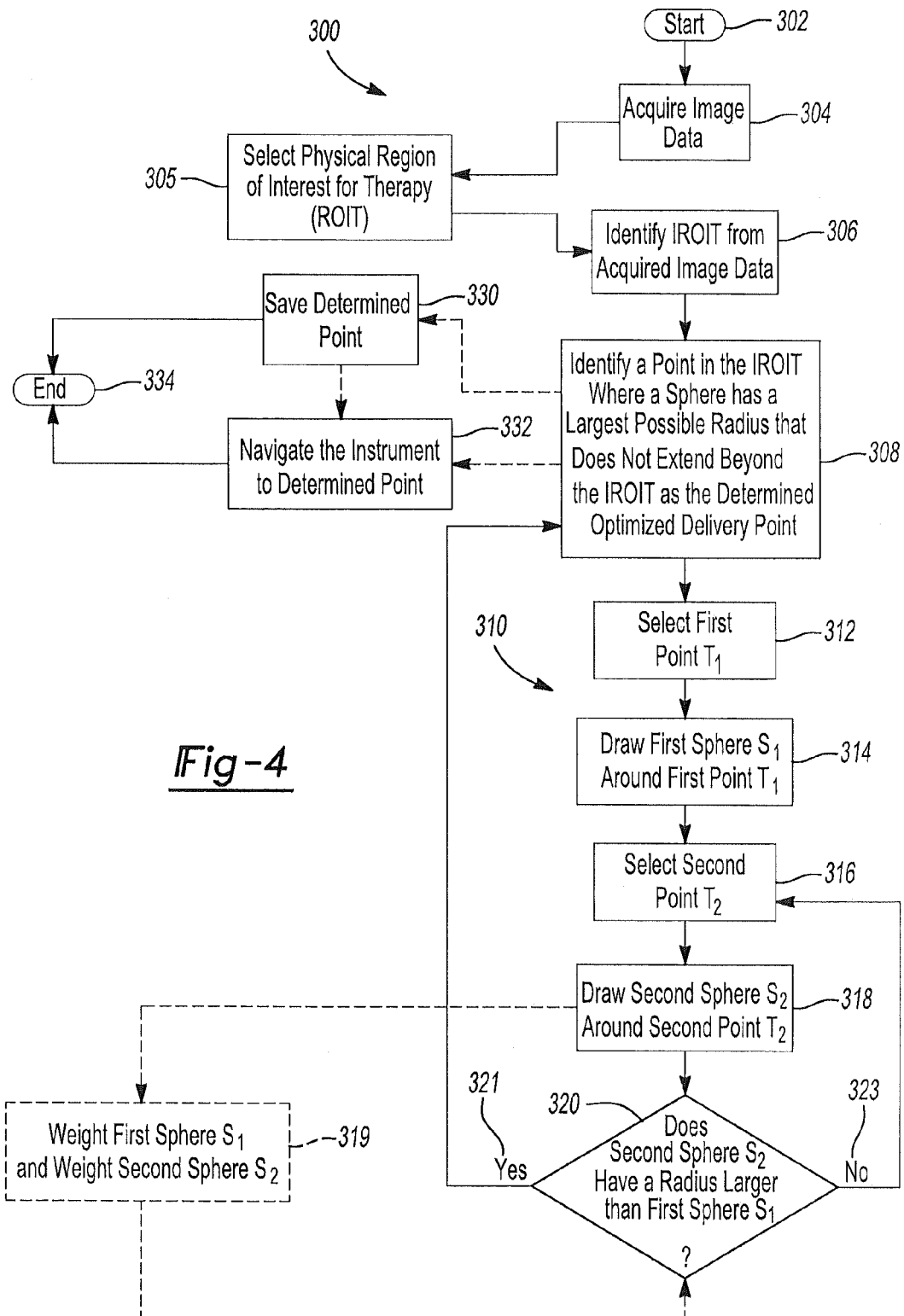
Figure 4A:
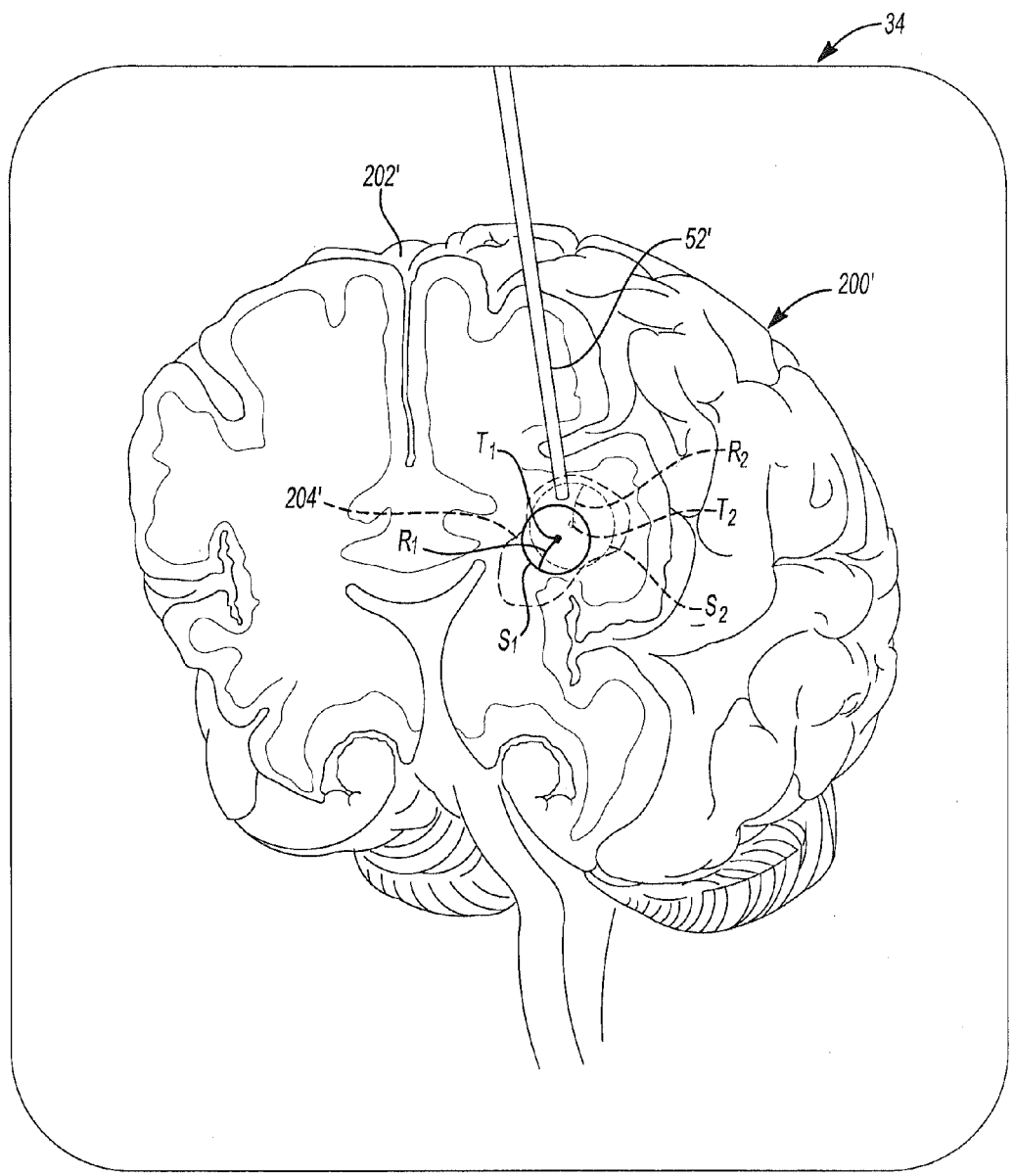
Figure 5:
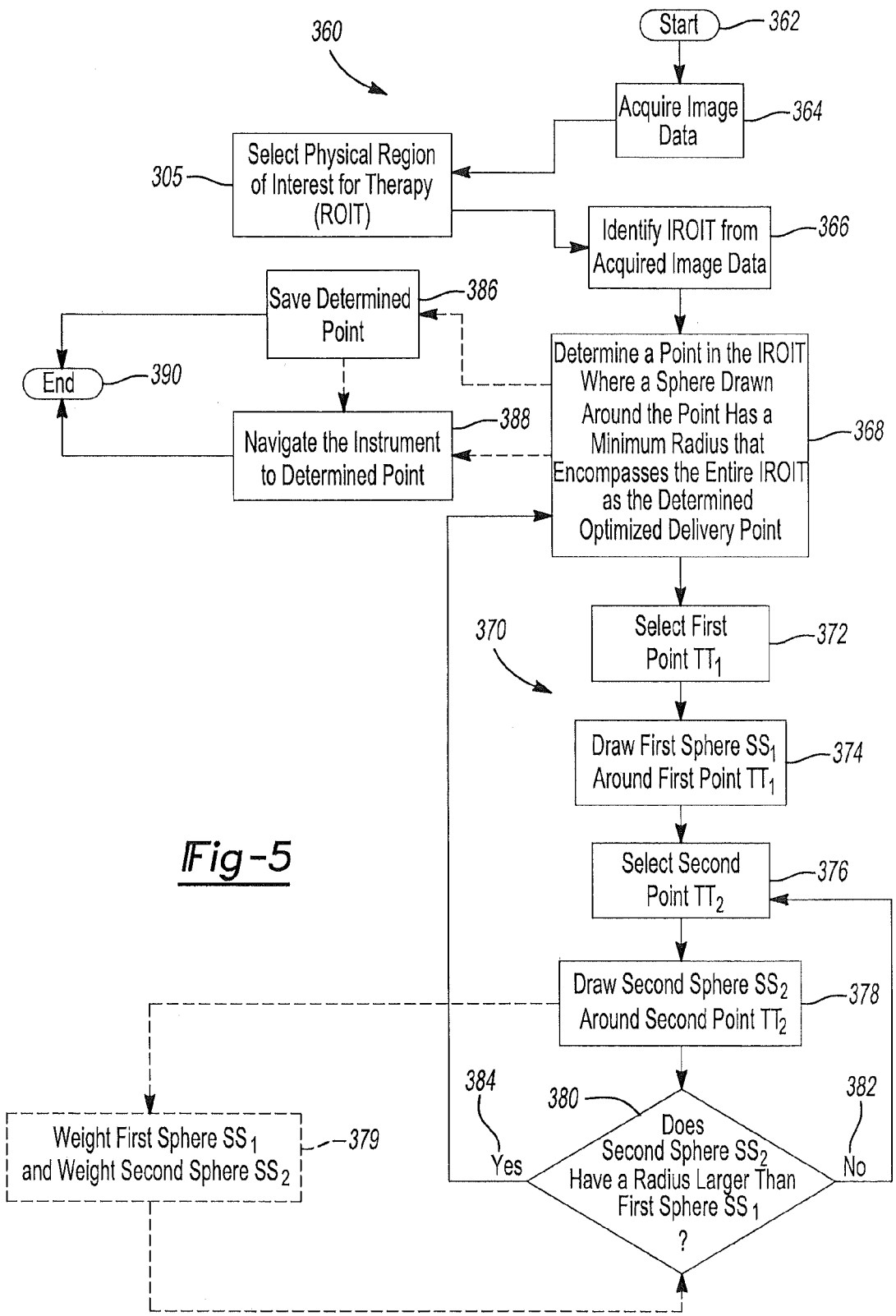
Figure 5A:
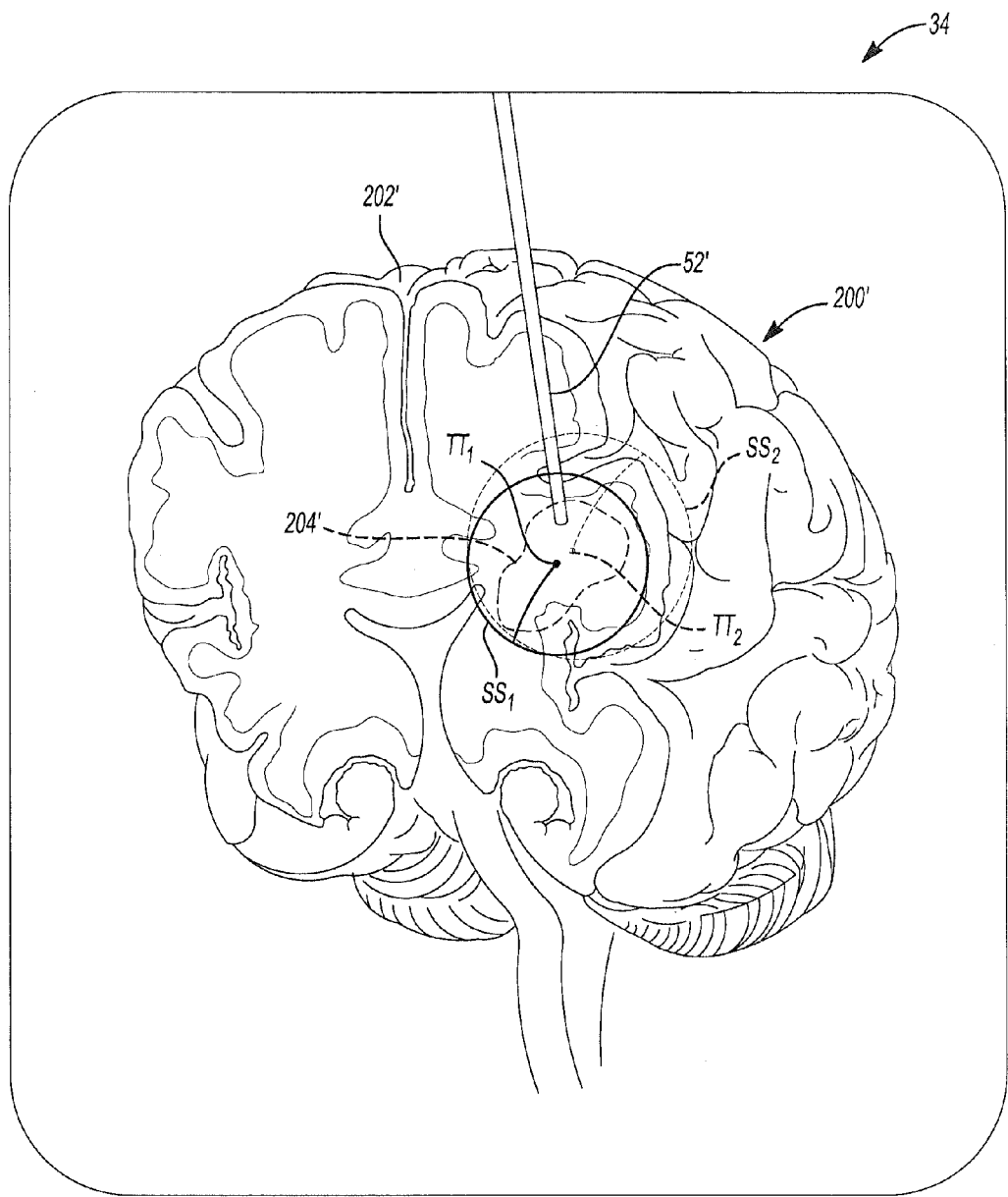

FIG. 2A' is a schematic illustration of a brain illustrating three-dimensions of a physical structure within the brain;

FIG. 2B' is an illustration of a display device displaying a segmented selected and a segmented unselected structure within the brain;

FIG. 3 is a flowchart illustrating an optimized point selection, according to various embodiments;

FIG. 3A is a graphical representation of the method illustrated in FIG. 3;

FIG. 4 is a flowchart illustrating an optimized point selection, according to various embodiments;

FIG. 4A is a graphical representation of the method illustrated in FIG. 4;

FIG. 5 is a flowchart illustrating an optimized point selection, according to various embodiments; and FIG. 5A is a graphical representation of the method illustrated in FIG. 5.

Corresponding reference numerals indicate corresponding parts throughout the several views of the drawings.

DETAILED DESCRIPTION

Example embodiments will now be described more fully with reference to the accompanying drawings.

A region of interest for therapy (ROIT) can be identified in a portion of a patient 14, such as in a brain 200 of the patient 14. The ROIT can be determined by a user manually, automatically with a processor, or combination of manual input and automatic determination. Within the ROIT an optimized delivery point or location 206 can be selected or determined for an introduction or initial delivery of a therapy. The therapy can include drug delivery. According to various methods, as discussed herein, the optimized delivery point can be determined based on image data 36 of the patient 14. Further, a navigation system 10 can be used to navigate or guide or a device 52 to the optimized delivery point.

Figure 1:
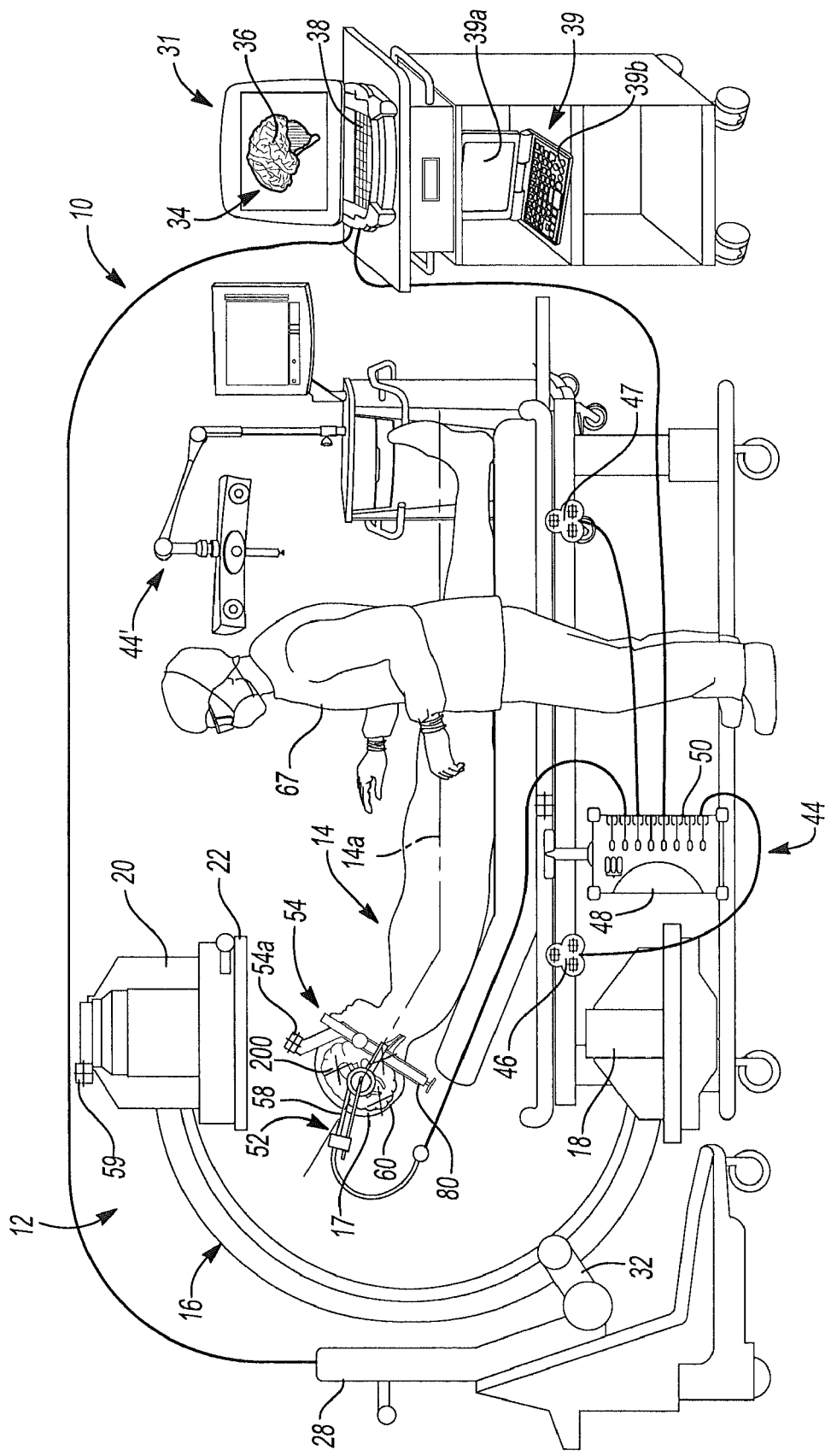
FIG. 1 is an environment view of a navigation system, according to various embodiments.

With reference to FIG. 1, the navigation system 10 can be used to track the location of the device 52, such as a drug delivery device, relative to the patient 14 to assist in the implementation of a plan or procedure, as discussed herein. It should be noted that the navigation system 10 may be used to navigate or track the device 52 including: catheters, probes, needles, leads, implants, etc. Moreover, the navigated device 52 may be used in any region of a body of the patient 14. The navigation system 10 and the various devices 52 may be used in any appropriate procedure, such as one that is generally minimally invasive, arthroscopic, percutaneous, stereotactic, or an open procedure. Although an exemplary navigation system 10 including an optional imaging system 12 are discussed herein, one skilled in the art will understand that the disclosure is merely for clarity of the present discussion and any appropriate imaging system, navigation system, patient specific data, and non-patient specific data can be used.

The navigation system 10 can include the optional imaging device 12 that is used to acquire pre-, intra-, or post-operative or real-time image data of a patient 14. The image data acquired with the imaging device 12 can be used as part of the optimization methods discussed herein. Alternatively various imageless systems can be used or images from atlas models can be used to produce patient images, such as those disclosed in U.S. patent application Ser. No. 10/687,539, filed Oct. 16, 2003, entitled "METHOD AND APPARATUS FOR SURGICAL NAVIGATION OF A MULTIPLE PIECE CONSTRUCT FOR IMPLANTATION", incorporated herein by reference. The optional imaging device 12 is illustrated as a fluoroscopic X-ray imaging device that may be configured as a C-arm 16 having an X-ray source 18, an X-ray receiving section 20, an optional calibration and tracking target 22 and optional radiation sensors 24. The calibration and tracking target 22 includes calibration markers (not illustrated). The C-arm is, however, only an example of the imaging device 12 and image data may also be acquired using other imaging devices, such as those discussed above and herein.

An optional imaging device controller 28 may control the imaging device 12, such as the C-arm 16, which can capture the x-ray images received at the receiving section 20 and store the images for later use. The controller 28 may also be separate from the C-arm 16 and can be part of or incorporated into a work station 31. The controller 28 can control the rotation of the C-arm 16. For example, the C-arm 16 can move in the direction of arrow 30 or rotate about a longitudinal axis 14a of the patient 14, allowing anterior or lateral views of the patient 14 to be imaged. Each of these movements involves rotation about a rotational or mechanical axis 32 of the C-arm 16. The movements of the imaging device 12, such as the C-arm 16 can be tracked with a tracking device 59.

In the example of FIG. 1, the longitudinal axis 14a of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray device that may be used as the optional imaging device 12 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, an O-arm® Imaging System (sold by Medtronic, Inc.)

Briefly, in operation, the C-arm 16 generates X-rays from the X-ray source 18 that propagate through the patient 14 and an optional calibration and/or tracking target 22, into the X-ray receiving section 20. Typically, the receiving section 20 includes an image intensifier that first converts the X-rays to visible light and a charge coupled device (CCD) video camera that converts the visible light into digital image data. Receiving section 20 may also be a digital device that converts X-rays directly to digital image data for forming images, thus potentially avoiding distortion introduced by first converting to visible light. The use of digital C-arms and calibration system are further described in U.S. Pat. App. Pub. No. 2004/00097805, published on May 20, 2004.

Two dimensional fluoroscopic images that may be taken by the imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg or cranium 17 and brain 200 may be appended together to provide a full view or complete set of image data of the leg or brain that can be later used to follow contrast agent, such as Bolus or therapy tracking. Multiple images can be reconstructed into a three-dimensional (3D) image.

The image data can then be forwarded from the C-arm controller 28 to a navigation computer and/or processor controller or work station 31 having a display device 34 to display image data 36 and a user interface 38. The work station 31 can also include or be connected to an image processor, navigation processor, and memory to hold instructions and data. The work station 31 can include an optimization processor, which can perform the methods discussed herein, or a separate optimization processor system 39 can be included. The optimization processor system 39 can also include a display 39a and a user input 39b. It will also be understood that the image data is not necessarily first retained in the controller 28, but may also be directly transmitted to the workstation 31, which can also include an image processor, navigation processor, memory, etc. Moreover, processing for the navigation system and optimization can all be done with a single or multiple processors.

The work station 31 or optimization processor 39 provides facilities for displaying the image data 36 as an image on the display device 34, saving, digitally manipulating, or printing a hard copy image of the received image data. The user interface 38, which may be a keyboard, mouse, touch pen, touch screen or other suitable device, allows a physician or user 67 to provide inputs to control the imaging device 12, via the C-arm controller 28, or adjust the display settings of the display device 34. The work station 31 may also direct the C-arm controller 28 to adjust the rotational axis 32 of the C-arm 16 to obtain various two-dimensional images along different planes in order to generate representative two-dimensional and three-dimensional images.

The optimization processor 39 can be provided in any appropriate format, such as a substantially portable format. The optimization processor 39 can be used in any appropriate portion of the methods discussed herein. For example, the optimization processor 39 can be separate from the navigation processor to allow for planning of the procedure.

Various calibration techniques can be used to calibrate the imaging device 12. Intrinsic calibration, which is the process of correcting image distortion in a received image and establishing the projective transformation for that image, involves placing the calibration markers in the path of the x-ray, where the calibration markers are opaque or semi-opaque to the x-rays. A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G.

Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the optional imaging device 12 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference), intra-vascular ultrasound (IVUS), intra-operative CT, single photo emission computed tomography (SPECT), planar gamma scintigraphy (PGS). Addition imaging systems include intraoperative MRI systems, such as the PoleStar® MRI system sold by Medtronic, Inc. Further imaging systems include the O-Arm® imaging system sold by Medtronic, Inc. The images may also be obtained and displayed in two, three, or four dimensions. Four-dimensional surface renderings of regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 12, as shown in FIG. 1, provides a virtual bi-plane image using a single-head C-arm fluoroscope as the optional imaging device 12 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, or probe introduced and advanced in the patient 14, may be superimposed in more than one view on display device 34 allowing simulated bi-plane or even multi-plane views, including two and three-dimensional views.

Four dimension (4D) image information can be used with the navigation system 10 as well. For example, the user 67 can use a physiologic signal, which can include Heart Rate (EKG), Breath Rate (Breath Gating) and combine this data with image data acquired during the phases of the physiologic signal to represent the anatomy at various stages of the physiologic cycle. For example, the brain pulses (and therefore moves) with each heartbeat. Images can be acquired to create a 4D map of the brain, onto which the atlas data and representations of the instrument can be projected. This 4D data set can be matched and co-registered with the physiologic signal (EKG) to represent a compensated image within the system. The image data registered with the 4D information can show the brain (or anatomy of interest) moving during the cardiac or breath cycle. This movement can be displayed on the display device 34 as the image data 36.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via image-fusion techniques and/or matching algorithms that are non-linear to match the distortion of anatomy based on the movements during the physiologic cycle. The combination of a the dynamic reference frame 54 and 4D registration techniques can help compensate for anatomic distortions during movements of the anatomy associated with normal physiologic processes.

With continuing reference to FIG. 1, the navigation system 10 can further include an electromagnetic navigation or tracking system 44 that includes a localizer, such as a coil array 46 and/or second coil array 47, the coil array controller 48, a navigation probe interface 50, a device 52 (e.g. catheter, needle, or instruments, as discussed herein) and a dynamic reference frame 54. Other tracking systems can include optical tracking systems 44' exemplary optical tracking systems include the StealthStation® Treon® and the StealthStation® Tria® both sold by Medtronic Navigation, Inc. The dynamic reference frame 54 can include a dynamic reference frame holder 80 and a removable tracking device 54a. Alternatively, the dynamic reference frame 54 can include a tracking device 54a that is formed integrally with the dynamic reference frame holder 80.

The tracking device 54a or any appropriate tracking device as discussed herein, can include both a sensor, a transmitter, or combinations thereof. Further, the tracking devices can be wired or wireless to provide a signal or emitter or receive a signal from a system. Nevertheless, the tracking device can include an electromagnetic coil to sense a field produced by the localizing array 46 or 47 or reflectors that can reflect a signal to be received by the optical localizer 44', 44". Nevertheless, one will understand that the tracking device can receive a signal, transmit a signal, or combinations thereof to provide information to the navigation system 10 to determine a location of the tracking device 54a, 58. The navigation system can then determine a position of the instrument or tracking device to allow for navigation relative to the patient and patient space.

The coil arrays 46, 47 may be those used in the Axiem® electromagnetic surgical navigation system sold by Medtronic Navigation, Inc. and may also be supplemented or replaced with a mobile localizer. The mobile localizer may be one such as that described in U.S. patent application Ser. No. 10/941,782, filed Sep. 15, 2004, and entitled "METHOD AND APPARATUS FOR SURGICAL NAVIGATION", herein incorporated by reference. As is understood the localizer array can transmit signals that are received by the tracking device 54a, 58. The tracking device 58 can then transmit or receive signals based upon the transmitted or received signals from or to the array.

Other tracking systems include acoustic, radiation, radar, infrared, etc. The optical localizer can transmit and receive, or combinations thereof. An optical tracking device can be interconnected with the instrument 52, or other portions such as the dynamic reference frame 54. As is generally known the optical tracking device 58a can reflect, transmit or receive an optical signal from the optical localizer 44' that can be used in the navigation system 10 to navigate or track various elements. Therefore, one skilled in the art will understand, that the tracking devices 54a, 58, and 59 can be any appropriate tracking device to work with any one or multiple tracking systems.

It should further be noted that the entire tracking system 44 or parts of the tracking system 44 may be incorporated into the imaging device 12, including the work station 31, radiation sensors 24 and optimization processor 39. Incorporating the tracking system 44 may provide an integrated imaging and tracking system. This can be particularly useful in creating a fiducial-less system. Any combination of these components may also be incorporated into the imaging system 12, which again can include a fluoroscopic C-arm imaging device or any other appropriate imaging device.

Each of the coils array 46, 47 can include a plurality of coils where each is operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 46 is controlled or driven by the coil array controller 48. The coil array controller 48 drives each coil in the coil array 46 in a time division multiplex or a frequency division multiplex manner. In this regard, each coil may be driven separately at a distinct time or all of the coils may be driven simultaneously with each being driven by a different frequency.

Upon driving the coils in the coil array 46 with the coil array controller 48, electromagnetic fields are generated within the patient 14 in the area where the medical procedure is being performed, which is again sometimes referred to as patient space. The electromagnetic fields generated in the patient space induce currents in the tracking device 54a, 58 positioned on or in the device 52. These induced signals from the tracking device 58 are delivered to the navigation probe interface 50 and subsequently forwarded to the coil array controller 48. The navigation probe interface 50 can also include amplifiers, filters and buffers to directly interface with the tracking device 58 in the device 52. Alternatively, the tracking device 58, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

Various portions of the navigation system 10, such as the device 52, the dynamic reference frame (DRF) 54, the instrument 52, are equipped with at least one, and generally multiple, EM or other tracking devices 58, that may also be referred to as localization sensors. The EM tracking devices 58 can include one or more coils that are operable with the EM localizer array 46 or 47. An alternative tracking device may include an optical sensor, and may be used in addition to or in place of the electromagnetic sensor 58. The optical sensor may work with the optional optical array 44'. One skilled in the art will understand, however, that any appropriate tracking device can be used in the navigation system 10. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

In brief, the EM tracking device 58 on the device 52 can be in a handle or inserter that interconnects with an attachment and may assist in placing an implant or in driving a portion. The device 52 can include a graspable or manipulable portion at a proximal end and the tracking device 58 may be fixed near the manipulable portion of the device 52 or at a distal working end, as discussed herein. The tracking device 58 can include an electromagnetic sensor to sense the electromagnetic field generated by the coil array 46 that can induce a current in the electromagnetic device 58. Alternatively, the tracking sensor 54a, 58 can be driven (i.e., like the coil array above) and the tracking array 46, 46a can receive a signal produced by the tracking device 54a, 58.

The dynamic reference frame 54 may be fixed to the patient 14 adjacent to the region being navigated so that any movement of the patient 14 is detected as relative motion between the coil array 46 and the dynamic reference frame 54. The dynamic reference frame 54 can be interconnected with the patient in any appropriate manner, including those discussed herein. This relative motion is forwarded to the coil array controller 48, which updates registration correlation and maintains accurate navigation, further discussed herein. The dynamic reference frame 54 may be any appropriate tracking sensor used as the dynamic reference frame 54 in the navigation system 10. Therefore the dynamic reference frame 54 may also be optical, acoustic, etc. If the dynamic reference frame 54 is electromagnetic it can be configured as a pair of orthogonally oriented coils, each having the same center or may be configured in any other non-coaxial or co-axial coil configurations.

Briefly, the navigation system 10 operates as follows. The navigation system 10 creates a translation map between all points in the image data generated from the imaging device 12 which can include external and internal portions, and the corresponding points in the patient's anatomy in patient space. After this map is established, whenever the tracked device 52 is used the work station 31 in combination with the coil array controller 48 and the C-arm controller 28 uses the translation map to identify the corresponding point on the pre-acquired image or atlas model, which is displayed on display device 34. This identification is known as navigation or localization. An icon representing the localized point or instruments is shown on the display device 34 within several two-dimensional image planes, as well as on three and four dimensional images and models.

To enable navigation, the navigation system 10 must be able to detect both the position of the patient's anatomy and the position of the instrument 52 or attachment member (e.g. tracking device 58) attached to the instrument 52. Knowing the location of these two items allows the navigation system 10 to compute and display the position of the instrument 52 or any portion thereof in relation to the patient 14. The tracking system 44 is employed to track the instrument 52 and the anatomy simultaneously.

The tracking system 44, if it is using an electromagnetic tracking assembly, essentially works by positioning the coil array 46 adjacent to the patient space to generate a magnetic field, which can be low energy, and generally referred to as a navigation field. Because every point in the navigation field or patient space is associated with a unique field strength, the electromagnetic tracking system 44 can determine the position of the instrument 52 by measuring the field strength at the tracking device 58 location. The dynamic reference frame 54 is fixed to the patient 14 to identify the location of the patient in the navigation field. The electromagnetic tracking system 44 continuously recomputes the relative position of the dynamic reference frame 54 and the instrument 52 during localization and relates this spatial information to patient registration data to enable image guidance of the device 52 within and/or relative to the patient 14.

Patient registration is the process of determining how to correlate the position of the instrument 52 relative to the patient 14 to the position on the diagnostic or pre-acquired images. To register the patient 14, a physician or user 67 may use point registration by selecting and storing particular points (e.g. fiducial points 60) from the pre-acquired images and then touching the corresponding points on the patient's anatomy with a pointer probe (not illustrated). The navigation system 10 analyzes the relationship between the two sets of points that are selected and computes a match, which correlates every point in the image data with its corresponding point on the patient's anatomy or the patient space. The points that are selected to perform registration are the fiducial markers or landmarks 60, such as anatomical landmarks. Again, the landmarks or fiducial points are identifiable on the images and identifiable and accessible on the patient 14. The landmarks 60 can be artificial landmarks 60 that are positioned on the patient 14 or anatomical landmarks that can be easily identified in the image data. The artificial landmarks, such as the fiducial markers 60, can also form part of the dynamic reference frame 54, such as those disclosed in U.S. Pat. No. 6,381,485, entitled "Registration of Human Anatomy Integrated for Electromagnetic Localization," issued Apr. 30, 2002, herein incorporated by reference.

The system 10 may also perform registration using anatomic surface information or path information as is known in the art (and may be referred to as auto-registration). The system 10 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, entitled "Method and Apparatus for Performing 2D to 3D Registration" filed on Aug. 20, 2003, hereby incorporated by reference.

Also, a substantially fiducial-less registration system can be provided, particularly if the imaging device 12 and the tracking system 44 are substantially integrated. Therefore, the tracking system 44 would generally know the position of the imaging device 12 relative to the patient 14 and fiducials may not be required to create registration. Nevertheless, it will be understood that any appropriate type of registration system can be provided for the navigation system 10.

In order to maintain registration accuracy, the navigation system 10 continuously tracks the position of the patient 14 during registration and navigation. Alternatively the patient 14 may be held immobile once the registration has occurred, such as with a head frame. Therefore, if the navigation system 10 did not track the position of the patient 14 or area of the anatomy, any patient movement after image acquisition would result in inaccurate navigation within that image. The dynamic reference frame 54 allows the electromagnetic tracking system 44 to register and track the anatomy. Because the dynamic reference frame 54 is rigidly fixed to the patient 14, any movement of the anatomy or the coil array 46 is detected as the relative motion between the coil array 46 and the dynamic reference frame 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images, atlas or 3D models may be registered relative to the patient and patient space, as discussed further herein. Generally, the navigation system allows the images on the display device 34 to be registered and accurately display the real time location of the various instruments and other appropriate items, such as the trackable pointer. In addition, the pointer may be used to register the patient space to the pre-acquired images or the atlas or 3D models. In addition, the dynamic reference frame 54 may be used to ensure that any planned or unplanned movement of the patient or the receiver array 46 is determined and used to correct the image on the display 34.

According to various embodiments, the DRF 54 can be fixed to the cranium 17 of the patient 14. To obtain a maximum reference it can be selected to fix the dynamic reference frame 54 in each of at least 6 degrees of freedom. Thus, the dynamic reference frame 54 can be fixed relative to axial motion X, translational motion Y, rotational motion Z, yaw, pitch, and roll relative to the portion of the patient 14 to which it is attached. Any appropriate coordinate system can be used to describe the various degrees of freedom. Fixing the dynamic reference frame relative to the patient 14 in this manner can assist in maintaining maximum accuracy of the navigation system 10.

In addition the dynamic reference frame 54 can be affixed to the patient in such a manner that the tracking sensor portion thereof is immovable relative to the area of interest, such as the cranium 17. A head band may form a part of the dynamic reference from 54. Further, a stereotactic frame, as generally known in the art, can be attached to the head band. Such systems for tracking and performing procedures are disclosed in U.S. patent application Ser. No. 10/651,267, filed on Aug. 28, 2003, and incorporated herein by reference.

The instrument 52 can be a DBS probe, a MER device, a catheter (e.g. a drug delivery catheter), etc. and each can include at least one of the tracking devices, such as the tracking device 58. The tracking device 58 can be any appropriate tracking device and can be formed in any appropriate manner such as the catheters described in pending U.S. patent application Ser. No. 11/241,837, filed on Sep. 30, 2005, incorporated herein by reference.

The instrument 52 can include the tracking device 58 at any appropriate position, such as near a distal end of the instrument 52. By positioning the tracking device 58 near the distal end of the instrument 52 knowing or determining a precise location of the distal end can be efficient. Determining a position of the distal end of the instrument 52 can be used to achieve various results, such as determining a precise position of the distal end of the instrument 52, a precise movement of the distal end of the instrument 52. It will be understood that knowing a position and moving the instrument 52 in a precise manner can be useful for various purposes, including those discussed further herein. Likewise, the instrument 52 can be directable according to various mechanisms and such as directing or pulling wires, directing or pulling signals, or any appropriate mechanism generally known in the art.

The instrument 52 can be navigated, as discussed above, to an optimized delivery point 206, FIG. 2A, within the patient 14. The optimized delivery point can be determined according to various methods, discussed herein, substantially automatically, as with the optimization processor 39, or with user input. The optimized delivery point 206 is a point within a region of interest for therapy (ROIT) within the patient 14. From the optimized delivery point 206 a therapy can be delivered, such as delivering a drug, delivering an electrical stimulation, delivery of stem cells or other tissue, or other appropriate therapies. The ROIT can be a physical location within the patient 14 and can be identified in image data of the patient 14. The instrument 52, including the tracking device 58, can be navigated to the optimized delivery point 206 in the patient 14.

The ROIT and the optimized delivery point 206 can be in any appropriate region of the patient 14. Discussed herein are specific examples within a brain 200 of the patient 14, such as a putamen 204, caudate 210, or an intrarcerebroventricular space. Other regions, however, can also be selected as the ROIT including cardiac regions, spinal regions, etc. Optimized delivery points can be selected within any of these appropriate regions according to the methods discussed herein.

In many regions in the patient 14, such as in the brain 200 or spinal regions, several tissue types are near or intertwined with one another. Also, a specific tissue type or volume to which a therapy is to be delivered may be bordered by other tissues or anatomical features selected to not receive a therapy. Accordingly, according to various embodiments of the methods discussed herein, the optimized delivery point 206 can be determined to assist in ensuring that a therapy is delivered to a selected tissue volume without impinging on other tissues types or volumes or only minimally impinging on other areas. According to various embodiments, a point a selected average distance from a border of a region for therapy, a point within a volume that encompasses a region for therapy, or a point within a volume that is within a region of therapy can be used to determine the optimized delivery point 206.

The brain 200 of the patient, or any other appropriate portion of the anatomy such as a spinal column, can include various substantially non-symmetrical structures. For example, the brain 200 can include a caudate 210, which can be related to other anatomical structures including the putamen 204. The caudate 210 can include various portions and the user 67 can identify or segment a selected portion of the caudate 210 for delivery of a therapy. For example, the user 67 can identify a head or anterior portion 212 of the caudate 210 as the region of interest for therapy, which can also be referred to as a selected segmented region. This may leave an unselected segmented region 214 of the caudate 210. The selected segmented region 212 can be selected for various purposes, such as effective or judicious delivery of the therapy. It will be understood that, as discussed herein, the optimized delivery point 206 can be identified within the selected segmented region 212 of the caudate 210 and may not achieve delivery to the unselected region 214 of the caudate 210. Accordingly, it will be understood, that the user 67 can predetermine or select a region within a region as a specific or segmented selected region of interest for therapy.

As illustrated in FIG. 2A, a brain 200 can be an organ in which a therapy will be delivered. The brain 200 includes various anatomical features or structures, such as a cortex structure 202, an intracerebroventricular (ICV) space, and a putamen 204. The navigation system 10, discussed above, can be used to navigate the instrument 52 into the brain 200 of the patient 14 to the optimized delivery point 206, as discussed herein.

The brain 200 is a three-dimensional object that defines a volume in space. Brain image data 200' can be acquired using various imaging modalities, such as MRI imaging. The brain image data 200', illustrated in FIG. 2B, can be illustrated in three-dimensions. The brain image data 200' can be used to determine the optimized delivery point 206, according to methods discussed herein.

The instrument 52 can have a delivery region or portion, such as a distal tip opening, that is placed at a delivery point for delivering a therapy to the brain 200 in the patient 14. To achieve an optimized therapy delivery to the patient 14, however, the instrument delivery region can be placed at the determined optimized delivery location 206. The instrument 52 can be navigated to the optimized point 206 with the navigation system 10, discussed above. The tracking device 56 can be connected or incorporated with the instrument 52 in any appropriate manner.

The optimized delivery location 206 can be a location in the patient 14 to achieve an optimized region of efficacy and has various attributes, as discussed further herein. The attributes of the optimized delivery location 206 are used to determine the position of the optimized delivery point 206 within the patient 14. Again, it will be understood, that the following discussion exemplary relates to delivery to the optimized delivery point in the putamen 204 or caudate 210 in the brain 200, other optimized points can be selected in other anatomical regions according to the methods discussed herein.

The optimized delivery location 206 can be selected based upon various information to achieve and optimize delivering of a therapy to the brain 200. The optimized delivery location 206 can be identified on the image data of the brain 200' as an optimized delivery icon 206' to identify the optimized delivery location in the brain image data 200'. The patient 14 can be registered to the image data 200' and the instrument 52 can be tracked relative to the patient 14 and image data 200'. An instrument icon 52' can be illustrated relative to the brain image data 200' to illustrate a navigated or tracked position of the instrument 52. This can allow the user 67 to move the instrument to the determined optimized delivery location 206 using the image data of the patient 14.

According to various embodiments, a method of determining an optimized point within a region is illustrated in a flowchart 250 in FIG. 3 and graphically represented in FIG. 3A. The method, briefly, entails determining a point in the image 200' that is a greatest distance from selected boundaries, regions, etc. The determined point can then be used or output as the optimized delivery location 206.

The method in the flowchart 250 can begin at start block 252. Image data can be acquired of the patient 14 in block 254. The image data acquired in block 254 can be of any appropriate portion of the patient 14, such as the brain 200. As discussed, the brain image data 200' is described as an example. In addition, the acquisition of the image data can be performed with any appropriate imaging technique. For example, magnetic resonance imaging (MRI) can be used to acquire the image data in block 254. The image data can be displayed on the display device 34 as the brain image data 200'. It will be understood, however, that the identification or process described in the flowchart 250 does not require the display of the image data acquired in block 254.

A region of interest for therapy (ROIT) can be selected in block 255. The ROIT can be selected at any appropriate time, even prior to image data acquisition. The ROIT can, for example, include the putamen 204 or caudate 210 in the brain 200. The flowchart 250 illustrates a method to select the optimized delivery location 206 within the putamen 204.

Selected therapies, such as pharmaceuticals, biological compounds, or other compounds, that are delivered by convection enhanced delivery can be selected to be delivered to the ROIT. Convection enhanced delivery can include the process disclosed in U.S. Pat. No. 5,720,720, incorporated herein by reference. The ROIT can include the entire or a selected portion of the putamen 204. The putamen 204 includes a mass and volume of gray matter. The delivery of the drug within the putamen 204, therefore, can be based upon delivery techniques and the selection a specific location of therapy delivery. Other volumes of delivery can include the intracerebroventricular (ICV) space, portions of the heart, etc.

The image data acquired in block 254 generally includes image data of at least the ROIT within the image data. An Image Region Of Interest for Therapy (IROIT) can be determined in the image data in block 256. The IROIT can be any appropriate region, such as a region in the image data that encompasses the physical (ROIT) in the patient 14. As discussed herein, the IROIT is the region in the image data that corresponds to the physical ROIT in the patient 14.

The determination of the IROIT in block 256 can be manual, automatic, or combination of manual and automatic selection. Manual selection of the IROIT can include the user 67, such as the surgeon, selecting a volume in the image data. For example, the image data acquired in block 254 can be displayed and the user 67 can select a volume within the image data. An automatic selection can include instructions executed by a processor, such as a processor of the navigation system 10 including the optimization processor 39 or any appropriate processor, to select the IROIT, such as the putamen 204'. A combination of automatic and manual selection can include the user 67 identifying one or more seed points or outlining a volume and a processor executing instructions to specify or include an entire region of the putamen 204' or any appropriate region. Algorithms or instructions to identify the region of interest can include any appropriate algorithms, including region growth or segmentation algorithms, marching borders, marching cubes or tetrahedron algorithms, or the like. Appropriate programs or algorithms include those used in the StealthStation® Treon® navigation system sold by Medtronic Navigation, Inc. having a place of business in Colorado, USA Leksell SurgiPlan® planning software (Elekta, AB), Amira® software platform (Visage Imaging, Inc.), and Mimics® medical imaging software (Materialise, NV).

Other automatic selections techniques of the IROIT can include registration of the acquired image data from block 254 to an atlas. An atlas can include a Tailerach atlas of a brain. The Tailerach atlas, or any appropriate atlas, can include a very detailed analysis and identification of a selected region of an anatomy, such as in the brain 200. The image data acquired in block 254 of the patient 14 can be registered to the atlas. By registering the image data acquired of the patient in block 254 to the atlas the regions identified in the atlas can be identified in the image data, such as the putamen. This is possible because once the image data is registered to the atlas identification of the IROIT, such as the putamen in the brain, can be performed by identifying the portion of the acquired image data that registers or is aligned with the identified region of the atlas.

Once the determination of the IROIT has been made in block 256, an identification or selection of test points within the IROIT can be performed in block 258. The identification of test points can include the identification of any appropriate portion of the image data acquired in block 254. For example, the identification of test points in block 258 can include the identification of regions, voxels, or points 257a and 257b, illustrated in FIG. 3A, within the IROIT. Voxels can include voxel data that is generated or acquired with the MRI. The voxels identified within the IROIT can include all of the voxels within the IROIT or a selected portion thereof. Alternatively, all points within the ROIT can be identified in block 258 including more than one point per voxel. It will be understood that various features may not be displayed for a user, such as removing the voxels on the display device. Any appropriate portion, therefore, can be selected as a test point or region.

The test points selected in block 258 can be selected by the user 67, manually, automatically, or as a combination. For example, the system can select all of the points within the IROIT as test points. The user 67 may manually select a number or region of test points in the IRIOT. The test points, as discussed herein, are then tested to determine the optimized delivery location 206.

Once test points are selected or identified in block 258, a measurement of a radius or line from each of the selected test points to at least one of a border of the ROIT, white matter outside of the ROIT, or other anatomical structure can be performed in block 260. The measurement of a radius can include a measurement of the distance from each selected test point to all borders or portions of the borders of the IROIT, identified white matter borders, or regions, or other anatomical structures along radius lines 257ra and 257rb, illustrated in FIG. 3A. The measurements can be made in the three dimensional space of the image data acquired in block 254. Accordingly, the radius measured in block 260 can be a three dimensional spatial location of the selected test point relative to at least one of the border of the IROIT, white matter, or other anatomical structures.

The measurement of the radius from each of the selected test points can be to all or one of any selected portions, such as the border of the IROIT, white matter, and the like. It will be further understood that a plurality of anatomical structures, for example, can be identified. The radius can be measured from each selected test point to any one or more of the plurality of anatomical structures. Similarly, a plurality of regions (e.g. areas at the IROIT border) can be identified on the border of the IROIT. A measurement or a radius from each of the selected test points to any one or more of the plurality of regions of the border of the IROIT can be measured.

Each point can have a plurality of radiuses measured relative to it. Each can, therefore, have an average of all of the measured radii. A test point with the determined greatest average radial distance can be based upon only an average of each of the radial measurements made, a weighted average of the radial measurements made in block 261, or any other appropriate calculation.

In a weighted average, however, the various radii measured can be weighted depending on characteristics selected and applied to each radius. For example, it can be selected that a greater radial distance from selected anatomical structures, regions of the border of the ROIT, or other structures are selected. For example, a radius measured from a ventricular space in the brain 200 can be weighted more than a radius measured from a portion of white matter. Also, a radius that is measured from a border of a segmented selected portion 212 that contacts the segmented unselected portion 214 can be weighted greater. Although the determined average can be any appropriate determined average, it can also provide that various portions, such as specific anatomical structures, are spatially preferred over others.

A determination of the optimized delivery point or location 206 can be made as the test point with the greatest average radial distance, either weighted in block 261 or not, in block 262. Once the optimized delivery point 206 (i.e. the test point with the greatest average radial distance) is determined in block 262, any appropriate selected procedure can follow. For example, the determined optimized delivery point 206 can be saved in an appropriate memory device in block 264. The optimized delivery point 206 can be saved for appropriate purposes, such as navigating the instrument 52 to the determined optimized delivery point 206 in block 266. Alternatively, the optimized delivery point 206 can be saved in block 264 for a later navigation or surgical procedure or planning and the method can end in block 268. It can be selected, therefore, that determining the optimized delivery point 206 with the greatest average radial distance in block 262 can be performed substantially intraoperatively or preoperatively and the method can then end in block 268. The method in the flowchart 250 can also be used for post-operative verification or identification. The method, according to any embodiment, can also be used pre-, intra-, or post-operatively for planning or verification.

For navigation, the optimized delivery point 206 can be illustrated as the icon 206' on the brain image data 200' to assist in navigating or performing a surgical procedure or therapy. Also, as illustrated in the method 250, the determination of the optimized delivery point 206 can be performed prior to a surgical procedure, such as any time after acquiring image data of the patient in block 254, to plan a selected procedure.

Although, the optimized delivery point 206 can be based on measuring a radius or distance in the method 250, the optimized delivery point 206, however, can be determined using alternative or additional techniques. As discussed below, a method of drawing spheres around test points to encompass a selected volume of the IROIT can be used. Drawing spheres or circles can be used to eliminate specific end points for radii or other appropriate purposes.

Turning to FIGS. 4 and 4A, according to various embodiments, a method of drawing spheres around test points to encompass a selected volume of the IROIT is illustrated in flowchart 300. According to the flowchart 300, the method or procedure can begin in start block 302. Image data can then be acquired in block 304. As discussed above, the acquisition of the image data can include inputting the image data from a source, directly acquiring image data of the patient 14, or other appropriate acquisition techniques. Accordingly, acquiring image data of the patient 14 does not require a direct or immediate acquisition of image data, but can include data that has been saved and is imported into a system that is executing the method illustrated in flowchart 300. In addition, the image data acquired of the patient 14 can be any appropriate image data. For example, for the discussion herein, MRI image data can be used. A ROIT can be selected in block 305 for various purposes, as discussed above.

Once the image data has been acquired in block 304 and the ROIT has been selected in block 305, an identification of an image region of interest for therapy (IROIT) in the acquired image data can be performed in block 306 that corresponds to the physical ROIT. The identification of the IROIT can be performed in any appropriate manner, as discussed above. Also, as discussed above, the IROIT can be the portion of the image data that includes the region for which a therapy is selected, such as in the putamen 204.

The IROIT can be identified manually by the user 67 identifying a region on the image data as the IROIT. The user can identify the region or volume in the image data using any appropriate technique, such as a touch screen, a pointer system, or the like to identify the IROIT. The user 67 can identify the putamen 204 as the IROIT in image data of the brain 200.

Identifying the IROIT in block 306 can also be performed substantially automatically or based upon a seed point or region identified by the user 67. The identification by a processor following an algorithm can segment the image data. Appropriate image segmentation algorithms are generally known, and can include input to identify or segment appropriate regions of the image data. For example, a threshold brightness can be identified and a segmentation program can identify or grow a region from the seed point or seed region to identify or select the entire IROIT. Appropriate segmentation computer software programs or algorithms include those used by various systems, such as the StealthStation® Treon® (Medtronic, Inc.), Leksell SurgiPlan® (Elekta, AB), Amira® (Visage Imaging, Inc.), and Mimics® (Materialise, NV). Also, as discussed above, registration of the image data to an atlas can be used to identify the IROIT.

Once the IROIT has been selected in block 306, a determination of the optimized delivery point 206 can be made in block 308. According to the method in flowchart 300, the optimized delivery point 206 can be a test point in the IROIT that is a center of a sphere that has a largest possible radius that does not extend outside of the IROIT. The spheres, however, can be also weighted, as discussed herein, so that the largest radius is not the sole selection criterion. It will be understood that any appropriate algorithm, such as search algorithms, can be used to determine optimized delivery point 206 from test points in the IROIT. An exemplary method is illustrated in sub-routine 310.

In the sub-routine 310, a first test point T1 can be selected in block 312. A first sphere S1 can be drawn around the first test point T1 within the IROIT in block 314. A second test point T2 can be selected in block 316. A second sphere S2 can be drawn around the second test point T2 within the ROIT in block 318.

Optionally, the first sphere S1 and the second sphere S2 can be weighted in block 319. As discussed above, the determination of an optimized point can be based upon a point that includes a sphere that is within the bounds of the IROIT. Optionally weighting the sphere in block 319 can precede the determination block 320 that determines whether the second sphere S2 has a radius larger than the first sphere S1. For example, a sphere that is near a ventricular space, even though completely within the IROIT, can be weighted lower than a sphere that is further from the ventricular space. It will be understood, however, that other weighting factors can be applied to the first sphere S1 and the second sphere S2.

A determination can then be made of whether a radius R2 of the second sphere S2 is larger than a radius R1 of the first sphere S1 in block 320. If the radius of the second sphere S2 is not larger than the first sphere S1, then the first test point T1 can be the determined point in block 308 by following the YES path 321. However, if the radius of the second sphere S2 is greater than radius of the first sphere S1, then the NO path 323 can be followed to select a different second test point T2 in block 316 and drawing a sphere in block 318 can be continued until test point is determined with a sphere with a largest radius is determined in block 320. As discussed above, the spheres S1 and S2 can be weighted, thus a simple geometrical determination may not always render the optimized point in block 308.

Once a test point is determined to be the optimized delivery point 206 in block 308, the optimized delivery point 206 can be saved in block 330. Saving the optimized delivery point 206 in block 330 can include saving the optimized delivery point 206 in a planning procedure system, such as in a memory system of the planning or optimization system 39. As discussed above, the planning or optimization system 39 can include a processor and memory system that can process or save the determined optimized delivery point 206. Alternatively, or in addition to saving the determined optimized delivery point 206, the instrument 52 can be navigated directly to the optimized delivery point 206 in block 332. Navigation of the instrument to the optimized delivery point 206 in block 332 can be performed with any appropriate navigation system or procedure, including that disclosed in U.S. patent application Ser. No. 11/683,796 filed on Mar. 8, 2007, and incorporated herein by reference. Navigation of the instrument to the determined optimized delivery point 206 in the ROIT can be performed by positioning or moving an instrument to the ROIT.

As discussed above, moving the instrument 52 to the optimized delivery point 206 within the ROIT, can include moving the instrument 52 to an optimized point within the putamen 204. As further illustrated above, for example in FIG. 2B, a display such as the display device 34, can display the image data 36 including an optimized delivery point icon 206' illustrating the optimized delivery point 206 and the icon 52' illustrating the position of the instrument 52 relative to the patient 14 and patient space.

Regardless of saving the determined optimized delivery point 206 in block 330, navigating an instrument 52 to the determined optimized delivery point 206 in block 332, or other appropriate measures, the method in the flowchart 300 can end in block 334. It will be understood, that the navigation of an instrument to the determined optimized delivery point 206 in block 332 is not necessarily required for determining the optimized delivery point 206 in the ROIT in block 308 as a part of the method in flowchart 300. Accordingly, the determined optimized delivery point 206 can be provided for any appropriate procedures, such as only planning a procedure, providing information to the user 67, or other appropriate purposes.

Various embodiments to determine the optimized delivery point 206 can be based on measuring a radius or distance from a plurality of test points to selected portions or a method of drawing spheres around test points to encompass a selected volume of the IROIT can be used. Alternatively, the optimized delivery point 206 can be a point that includes the attributes of being the center of a sphere that encompasses at least the entire ROIT while including as little as possible other surrounding areas. The point can be identified in the ROIT according to a method in a flowchart 360 illustrated in FIG. 5.

With reference to FIGS. 5 and 5A, the method of identifying the optimal delivery point 206 can begin in start block 362. Image data can be acquired in block 364. The type of image data, such as MRI or fluoroscopic image data, can be acquired in any appropriate manner, such as those described above. As a particular example, MRI image data can be acquired of the patient 14 and analyzed according to the method in the flowchart 360, discussed further herein. The image data can be acquired and saved for analysis in a planning procedure or can be acquired and used during an operative procedure to determine and plan a procedure relative to the optimal location 206. A physical ROIT can be identified in the patient 14 in block 365, as discussed above, and can include the putamen 204 in the brain 200.

Once the image data is acquired in block 364, identification of the IROIT in the acquired image data can be performed in block 366. The selection of the IROIT can be performed in any appropriate manner, including those discussed above. Again, the IROIT can include the area or region to which a therapy will be delivered, such as the putamen 204. For example, a manual identification of the IROIT can be made by the user 67. Alternatively, or in addition thereto, an algorithm can be used to segment the image data either with a seed point identified with the user 67 or otherwise. Alternatively, or in addition thereto, the image data can be registered to an atlas of a region of the patient 14, as discussed above.

Once the IROIT has been identified in the image data in block 336, the optimized delivery point 206 can be determined as one test point in the IROIT that is a center of a sphere that has the smallest radius that encompasses the entire IROIT in block 368. Drawing a sphere that encompasses the entire IROIT from a point within the IROIT may require that the sphere encompass regions that are outside of the IROIT. This is alternative to the process discussed in the flowchart 300 where the sphere is to be contained only within the IROIT. Accordingly, according to various embodiments, it can be selected to ensure that the optimized delivery point 206 is selected based on delivering a therapy that is maintained or contained within the ROIT, even if a portion of the ROIT is not affected, or ensuring that the entire ROIT will be affected by a therapy even if other areas are also affected. Determining a point where a sphere encompasses more than an IROIT may be used to ensure that the entire ROIT is affected by a therapy.

It will be understood that any appropriate process can be used to determine the optimized delivery point 206 in block 368. Appropriate processes can include the exemplary subroutine 370. The exemplary sub-routine 370 can include selecting a first test point TT1 in block 372. Once the first test point TT1 is selected, drawing a first sphere SS1 to encompass all of the IROIT from point TT1 can be drawn in block 374. A second test point TT2 can be selected in block 376 and a second sphere SS2 can be drawn to encompass the entire IROIT in block 378.

After the first sphere SS1 and the second sphere SS2 are drawn or determined, the first sphere SS1 and the second sphere SS2 can be weighted in block 379. As discussed above, the spheres SS1 and SS2 can be drawn to encompass at least all of the IROIT. Accordingly, the spheres can be weighted on the amount of overlap of an undesired space, such as the ventricular space. The ventricular space in the brain 200 is a space where if a drug is delivered it may not substantially affect the brain 200 in any therapeutic manner. Accordingly, delivering a drug or any portion of a drug to the ventricular space can be substantially inefficacious. Accordingly, weighting a sphere that overlaps the ventricular space the least as the highest weighted sphere can be appropriate. It will be understood, however, that the spheres SS1 and SS2 can be weighted in any appropriate manner, such as overlapping in the undesired space including only the space outside of the IROIT.

A determination can then be made as to whether the radius of the first sphere SS1 is less than the radius of the second sphere SS2 in determination block 380. It will be understood, however, that the determination in block 380 can be based on more than simply a geometric determination. As discussed above, the spheres SS1 and SS2 can be weighted according to various criteria. If it is determined that the radius of the second sphere SS2 is less than the radius of the first sphere SS1, then the NO routine 382 can be followed to select a further test point in block 376. The iteration can then continue until the radius of a new sphere is not less than a radius of a previous sphere. When the radius of the new sphere is greater than the radius of the previous sphere then the YES routine 384 can be followed as having determined the optimized delivery point 206 in block 368 as the center of the sphere with the smallest radius.

Once the optimized delivery point 206 has been determined in block 368, the optimized delivery point 206 can be saved in block 386. As discussed above, the optimized delivery point 206 can be saved in any appropriate memory system, such as a memory system of the optimization and planning processor system 39. Alternatively, or in addition to saving the determined optimized delivery point 206, an instrument can be navigated to the determined optimized delivery point 206 in block 388. It will be understood, as discussed above, that the determined optimized delivery point 206 in block 368 can be performed prior to a procedure, such as in planning a procedure, or intraoperatively while the procedure is being performed. The method can then end in block 390.

It will be understood that defining or measuring radii or spheres are merely exemplary geometrical measurements or constructions. Other appropriate measurements or shapes can be used, such as triangles, etc. In addition, multiple points may be identified as multiple optimized delivery points 206 to achieve the best fit to create a selected volume of efficacy. In other words, more than one delivery point may be used to generate a non-spherical shape that best fits the ROIT. Non-spherical shapes can include user or processor morphed shapes that can begin with spheres, cubes, etc. Finally, the shape or measurements used may depend upon the instrument used to deliver the therapy, type of therapy, etc. Accordingly, the user or an automatic selection can be made to select the shape or measurement to determine the optimized point 206.

Selecting the optimized point of delivery 206 can be selected to assist in delivering therapy only to a selected region within the patient 14. Also, it can be used to ensure a volume of efficacy, as discussed herein. Selecting the point 206 based on a geometric location can be based upon the theory and analysis of drug delivery or therapy delivery discussed below. In addition, the optimized delivery point 206 is a point that is determined to meet the specified attributes, such as to generate a sphere of therapy in a selected region. Accordingly, the optimized delivery point 206 is provided as guidance to the user 67 and can be augmented by the user 67 for various purposes.

Delivery of a therapy into the patient 14 can include delivery of a pharmaceutical including a molecule or compound of interest. The molecule of interest can include a selected physiological effect of the patient 14 that is selected or desired. Targeted drug delivery into a region of the brain 200, such as the parenchyma or putamen 204 of the brain, uses the mass transport characteristics of the infusate exiting out of the catheter (as delivered by a pump) to enhance the pharmacological effect of the drug by producing a meaningful physiological change on a local level. Selected delivery of a pharmaceutical can require or be accomplished with an appropriate understanding and implementation of physics, physiology, and pharmacology.

Regarding the physics of delivering drugs, if the drug is delivered to the parenchyma, it is essentially delivered directly to the interstitium, or extracellular space (ECS), of the neuropil. In this manner, the brain 200 can be thought of as porous media, where the ECS is the "pores" of the brain 200. When locally delivered by pumped infusion, the drug moves through these pores by two mechanisms or methods: diffusion and convection.

Diffusion is the rate that the drug moves of its own accord—a "random walk"—and is generally a slow process. The "driving force" of this flux is the concentration gradient that exists between the infusate in the catheter and ECS. The second source of drug flux in this combination product is convection, or the movement of the infusate as it is being pumped from the catheter outlet. This effect, generally known as "convection-enhanced delivery" (CED), is a much greater source of flux than diffusion alone. CED is a motive force causing the drug to have a larger distribution. This can be the main physical phenomenon used to distribute the drug, and can be characterized by relevant hydraulic characteristics that effect this distribution, including hydraulic conductivity, tissue anisotropy and viscosity of the infusate.

Regarding physiology in targeted drug delivery includes consideration of the anatomy of brain, or other appropriate anatomical region, and the physiological processes that are actively removing the drug from the ECS of the brain. Targeted drug delivery, by definition, achieves a local distribution. Thus, it is of primary importance to understand the anatomy in order to achieve optimal delivery of the drug. Additionally, the pharmacokinetics of local drug delivery—specifically, bulk flow clearance from the ECS can be considered. Comparable to clearance from the blood stream, bulk flow clearance is the active physiological process that clears large molecules from the ECS into the perivascular space of the brain. From the perivascular space, according to one theory, the drug continues to be removed from the brain by entering into the perivascular channels of the leptomininges and, finally, into the cervical lymph nodes.

A third consideration in targeted drug delivery is the characteristics of the drug itself or pharmacology, specifically its pharmacodynamic properties. In particular, the rate at which the drug interacts with the environment of the ECS directly effects the resultant chronic distribution of the drug. In particular, the following pharmacodynamic properties are intrinsically important, as they remove the drug from the ECS space: disassociation constant and binding capacity, drug internalization rate, and drug immunogenecity and metabolism.

Also to be considered is the volume of efficacy of a targeted drug delivery which is defined as the region of the brain where the locally administered drug achieves a tissue concentration high enough to elicit a meaningful physiological effect. Accordingly, the methods illustrated in the flowcharts 250, 300, and 360 can be used in defining an area that takes into account the physics, physiology, and pharmacology of a drug, including the molecule of interest, when determining a volume and a delivery point for achieving the volume of efficacy in the ROIT. Also, as discussed above, the geometric identification of a point in the image data can be used to identify a region that would best be covered by a spherical delivery of a drug. Thus, the delivery system can be used to deliver a substantially spherical volume of efficacy based on physics, physiology, and pharmacology of a drug in the patient 14.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of determining a delivery location within a volume, comprising:
   selecting a physical region within the volume for a drug delivery;
   determining a volume of efficacy for the drug within the physical region where the delivered drug achieves a tissue concentration to elicit a meaningful physiological effect in the selected physical region;
   acquiring image data of the volume;
   determining an image region of therapy in the image data that is the physical region within the image data; and
   determining an optimized delivery point within the selected physical region to achieve the volume of efficacy wherein determining an optimized delivery point includes operating a processor to execute instructions for:
   identifying a plurality of points within the image region of therapy and a plurality of line segments radially extending from each point of the plurality of points,
   measuring a length of each line segment of the plurality of line segments from each point, assigning a weight to each line segment based at least on a location of a second end of each line segment relative to at least one of a border of the image region of therapy or a structure in the image data, determining a weighted average length of the plurality of line segments extending from each point, and outputting the optimized delivery point based on the determined weighted average of the line segments extending from each point.

2. The method of claim 1, further comprising:

displaying the outputted optimized delivery point superimposed on the image data; and navigating an instrument to the outputted optimized delivery point.

3. The method of claim 1, further comprising:

segmenting the image data into at least a selected segmented region relating to the selected physical region and an unselected segmented region relating to an unselected physical region.

4. The method of claim 3, wherein determining an optimized delivery point within the selected physical region further includes determining the optimized point to achieve the volume of efficacy substantially only in the selected segmented region, wherein assigning the weight to each line segment includes assigning a greater weight to a line segment that contacts a border of the selected segmented region.

5. The method of claim 1, wherein assigning a weight to each line segment based at least on the location of the second end of each line segment relative to the border of the image region of therapy includes assigning a greater weight to the line segment that has the second end further from white matter;

wherein determining an optimized delivery point further includes:

determining which point of the identified plurality of points has a maximum determined weighted average length of the plurality of line segments.

6. The method of claim 1, wherein each point of the plurality of points within the image region of therapy is a center of a sphere that is completely within the image region of therapy, and wherein each line segment is a radius of at least one sphere of a plurality of spheres based on the identified plurality of points; and wherein determining an optimized delivery point further includes determining which one sphere of the plurality of spheres has a maximum radius.

7. The method of claim 1, wherein each point of the plurality of points within the image region of therapy is a center of a sphere that completely encompasses the image region of therapy and wherein each line segment is a radius of at least one sphere of a plurality of spheres based on the identified plurality of points; and wherein determining an optimized delivery point further includes determining which one sphere of the plurality of spheres has a minimum radius.

8. A method of determining an optimized location for delivering a compound of interest within a brain, comprising:

selecting a physical region within the brain for the compound of interest delivery;

selecting an instrument for the compound of interest delivery;

determining a volume of efficacy for the compound of interest, including evaluating the interaction of the compound of interest within the selected physical region within the brain;

acquiring image data of the brain;

identifying an image region of therapy that is a representation in the acquired image data of the selected physical region; and determining at least a single optimized delivery point within the image region of therapy to achieve the volume of efficacy at least within a portion of the selected physical region, including operating a processor to automatically execute instructions after identifying the image region of therapy, wherein the instructions include:

identifying a plurality of points within the image region of therapy;

determining a plurality of line segments radially extending from each point of the plurality of points to at least one of a surface of the image region of therapy or structures outside of the image region of therapy;

measuring a length of each line segment; and determining an average length of the plurality of line segments extending from each point;

wherein the single optimized delivery point is based at least on the determined average length of the plurality of line segments extending from each point, and superimposing at least the determined single optimized delivery point as an icon on the acquired image data.

9. The method of claim 8, wherein identifying an image region of therapy includes segmenting the image data by at least selecting a seed point.

10. The method of claim 8, wherein determining the optimized delivery point is substantially automatically determined by operating the processor after a user selects the physical region.

11. The method of claim 8, wherein the optimized delivery point includes one point of the plurality of points with a determined maximum average length of the plurality of line segments.

12. The method of claim 11, wherein the determined maximum average line segment length includes weighting each of the sub-plurality of line segment lengths extending from each point.

13. The method of claim 8, wherein each point of the identified plurality of points is a center of a sphere that is completely within the image region of therapy;

wherein each line segment is a radius of at least one sphere of a plurality of spheres based on the identified plurality of points; and wherein determining the optimized delivery point further includes determining which sphere of the plurality of spheres has a maximum radius.

14. The method of claim 13, wherein determining which sphere of the plurality of spheres has the maximum radius includes weighting each of the plurality of spheres.

15. The method of claim 8, wherein each point of the identified plurality of points within the image region of therapy is a center of a sphere that completely encompasses the image region of therapy;

wherein each line segment is a radius of at least one sphere of a plurality of spheres based on the identified plurality of points; and wherein determining the optimized delivery point further includes determining which sphere of the plurality of spheres has a minimum radius.

16. The method of claim 15, wherein determining which sphere of the plurality of spheres has a minimum radius includes weighting each sphere of the plurality of spheres.

17. The method of claim 8, further comprising:

segmenting the selected physical region into a segmented selected region and a segmented unselected region;

wherein determining an optimized delivery point includes determining an optimized delivery point only to the segmented selected region.

18. A system to determine a delivery location within a volume, comprising:
a storage system operable to store acquired image data of the volume;
an input device operable to input a selected physical region within the volume for compound of interest delivery;
an instrument configured to be positioned within the volume to deliver the compound of interest;
a processor operable to execute instructions to identify an image region of therapy that is a representation of the selected physical region, wherein the processor is further operable to execute instructions to determine an optimized delivery point within the image region of therapy to position at least a portion of the instrument to achieve a volume of efficacy at least within a portion of the selected physical region, wherein the instructions include:
identifying a plurality of points within the image region of therapy;
determining a plurality of line segments radially extending from each point of the plurality of points to at least one of a surface of the image region of therapy or structures outside of the image region of therapy;
measuring a length of each line segment; and
determining an average length of the plurality of line segments extending from each point;
wherein the optimized delivery point is based at least on the determined average length of the plurality of line segments extending from each point; and
an output device operable to output the determined optimized delivery point relative to the acquired image data.

19. The system of claim 18, wherein the output device includes a display device;
wherein the display device is operable to display the acquired image data and an icon superimposed on the acquired image data as the determined optimized delivery point.

20. The system of claim 18, further comprising:
an imaging system operable to acquire three dimensional image data of the volume.

21. The system of claim 18, further comprising:
a navigation system having a localizer and a trackable portion;
wherein the navigation system is operable to track the trackable portion and superimpose an icon representing a position of the trackable portion relative to the image data viewable with the output from the output device.

22. The system of claim 21, wherein the trackable portion includes the instrument;
wherein the icon is operable to represent a delivery portion of the instrument.

23. The method of claim 1, wherein each of line segments extends from one point of the identified plurality of points to at least one of a surface of the image region of therapy or structures outside of the image region of therapy.

24. The method of claim 23, wherein assigning weights to each line segment is further based on at least one of assigning a different weight to each line segment based on difference of a length of the second end point of each line segment relative to the surface of the image region of therapy, a difference of length of the second end point of each line segment from each point to a portion of white matter, or combinations thereof.

25. The method of claim 8, wherein the determined optimized delivery point includes one point that has the plurality of line segments with a minimum average length.

26. The method of claim 25, further comprising:
weighting each line segment of the plurality of line segments from each point prior to determining the average length of each plurality of line segments from each point, wherein the determined average length of the plurality of line segments can be augmented by the weighting.

27. The method of claim 8, wherein determining a volume of efficacy for the compound of interest, further includes evaluating at least one of a mass transport for the compound of interest, pharmacokinetics for the compound of interest in the selected physical region, or pharmacodynamics for the compound of interest in the selected physical region.

28. The method of claim 18, wherein to achieve the volume of efficacy at least within a portion of the selected physical region the processor is operable to further execute instructions to evaluate at least one of a mass transport for the compound of interest, pharmacokinetics for the compound of interest in the selected physical region, or pharmacodynamics for the compound of interest in the selected physical region.

* * * * *

UNITED STATES PATENT AND TRADEMARK OFFICE
CERTIFICATE OF CORRECTION

| | | |
|---|---|---|
| PATENT NO. | : 8,335,552 B2 | Page 1 of 1 |
| APPLICATION NO. | : 12/431108 | |
| DATED | : December 18, 2012 | |
| INVENTOR(S) | : Stiles | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 477 days.

Signed and Sealed this
Second Day of December, 2014

Michelle K. Lee
*Deputy Director of the United States Patent and Trademark Office*